US006592555B1

United States Patent
Wen-Pi et al.

(12) United States Patent
(10) Patent No.: US 6,592,555 B1
(45) Date of Patent: Jul. 15, 2003

(54) SYRINGE DEVICE

(76) Inventors: Wang Wen-Pi, 4F, No. 357, Da-Na Road, Su Lin, Taipei City (TW); Lin Te-Fa, 11F-2, No. 43, Chai-I Street, Taichung City (TW)

( * ) Notice: Subject to any disclaimer, the term of this patent is extended or adjusted under 35 U.S.C. 154(b) by 487 days.

(21) Appl. No.: 09/599,894

(22) Filed: Jun. 23, 2000

(51) Int. Cl.[7] .................................................. A61M 5/00
(52) U.S. Cl. ........................ 604/181; 604/187; 604/195; 604/196; 604/201; 604/221; 604/218; 128/919; 128/753
(58) Field of Search ................................. 604/181, 187, 604/195, 196, 218, 201, 221; 128/919, 753

(56) References Cited

U.S. PATENT DOCUMENTS

| | | | | |
|---|---|---|---|---|
| 2,880,725 A | * | 4/1959 | Kendall | 604/196 |
| 2,887,108 A | * | 5/1959 | Kendall | 604/196 |
| 3,306,290 A | * | 2/1967 | Weltman | 604/197 |
| 4,986,278 A | * | 1/1991 | ravid et al. | 128/753 |
| 5,007,903 A | * | 4/1991 | Ellard | 604/195 |
| 5,013,301 A | * | 5/1991 | Marotta, Jr. et al. | 604/197 |
| 5,522,804 A | * | 6/1996 | Lynn | 604/191 |
| 5,674,203 A | * | 10/1997 | Lewandowski | 604/197 |
| 5,769,825 A | * | 6/1998 | Lynn | 604/191 |
| 5,788,677 A | * | 8/1998 | Botich et al. | 604/195 |
| 2001/0053886 A1 | * | 12/2001 | Caizza | 604/110 |

* cited by examiner

*Primary Examiner*—Thomas Denion
*Assistant Examiner*—Theresa Trieu
(74) *Attorney, Agent, or Firm*—Charles E. Baxley

(57) ABSTRACT

A syringe device includes a barrel in which a stopper connected to a plunger is movably received, and an engaging section extends from an end of the barrel. A base member is disengagably received in an engaging section of the barrel and a needle cannula is connected to the base member. The stopper has a protrusion which is engaged with a recess in the base member when the stopper is moved to a extreme position when pushing the plunger. The base member is disengaged from the engaging section and moved into the barrel together with the stopper when the plunger is pulled backward. A pushing device is located between the base member and the stopper to tilt the base member in the barrel.

9 Claims, 9 Drawing Sheets

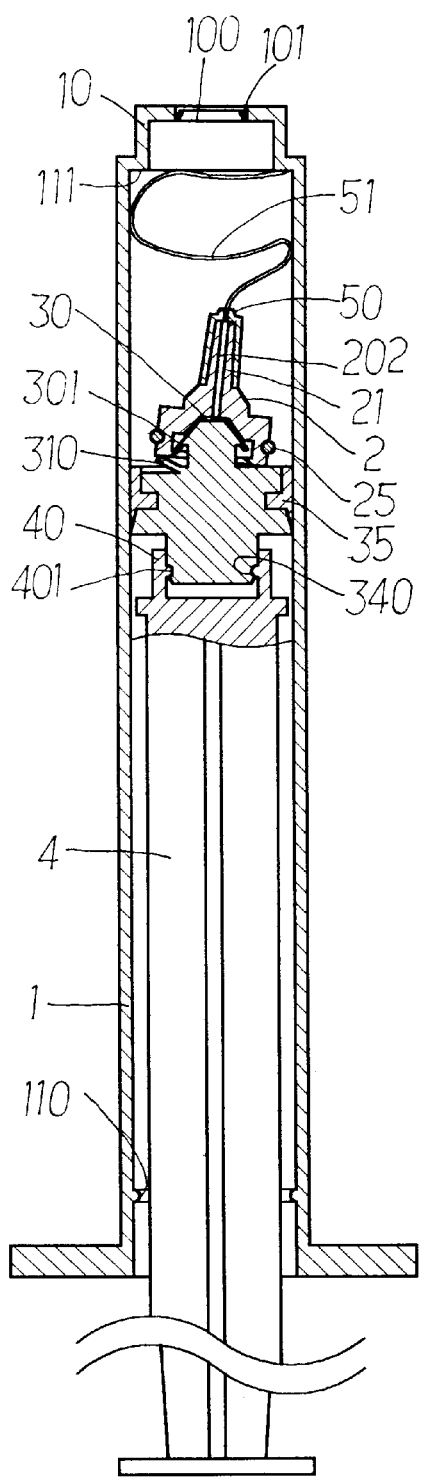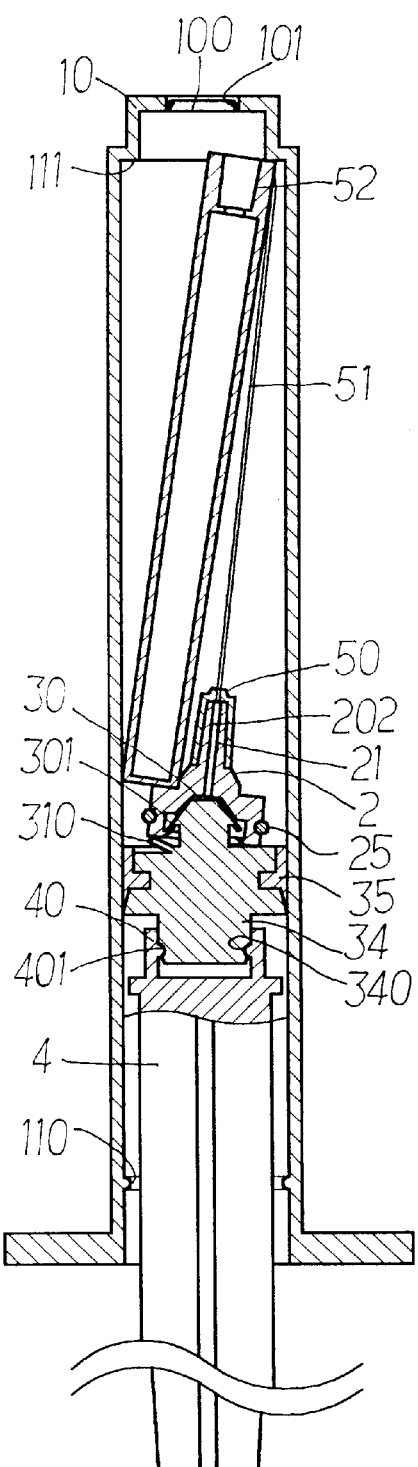
FIG·10  FIG·11

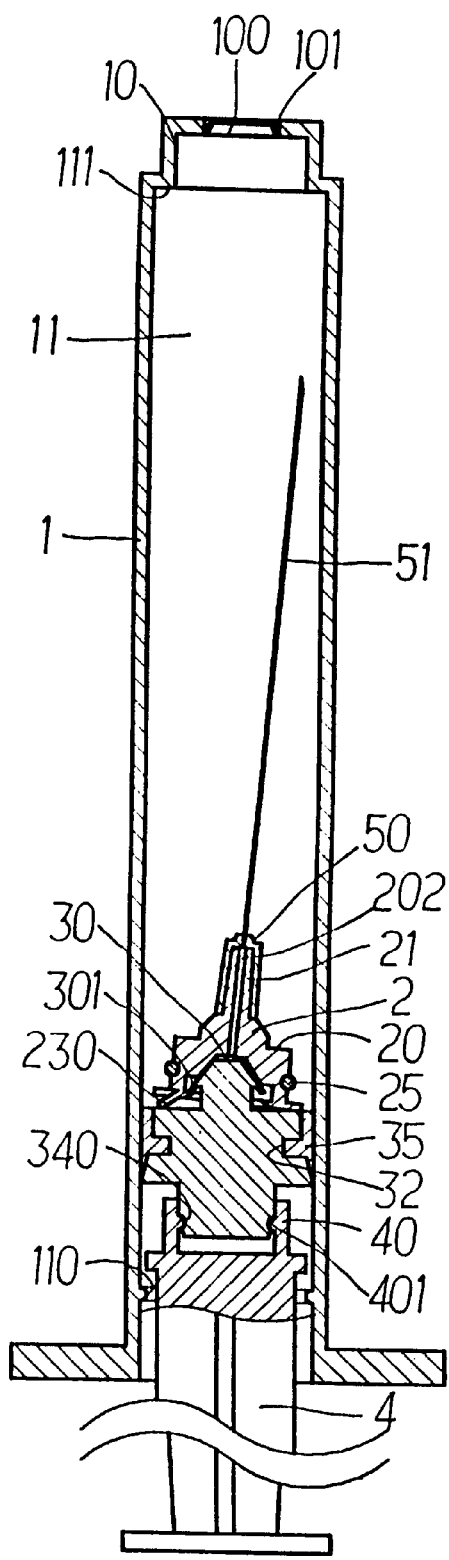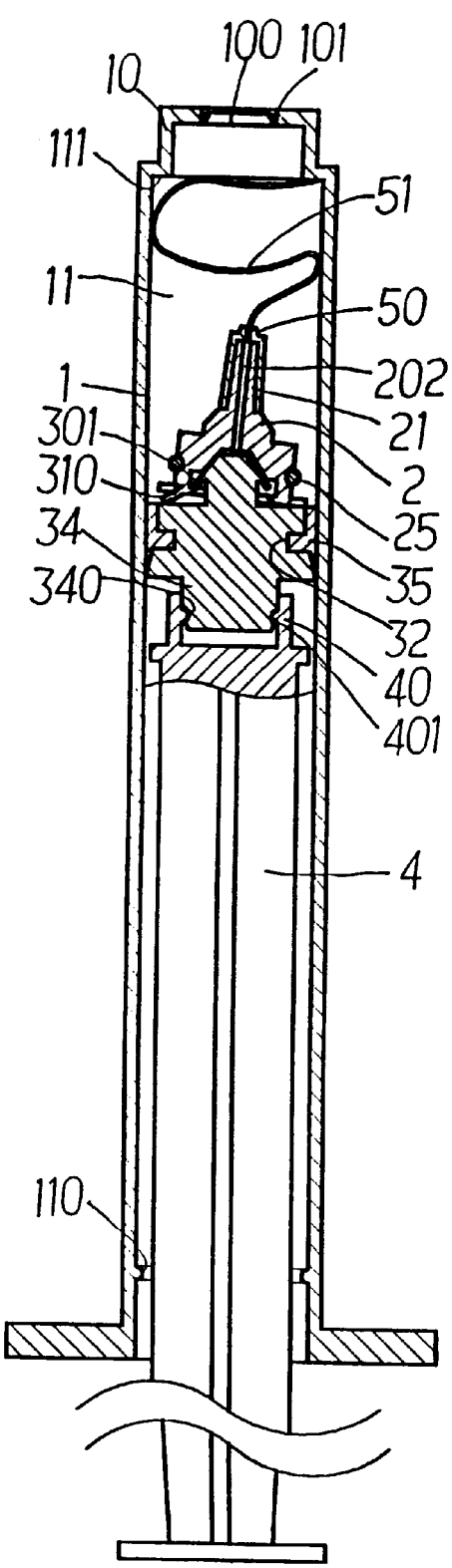
FIG·12　　　FIG·13

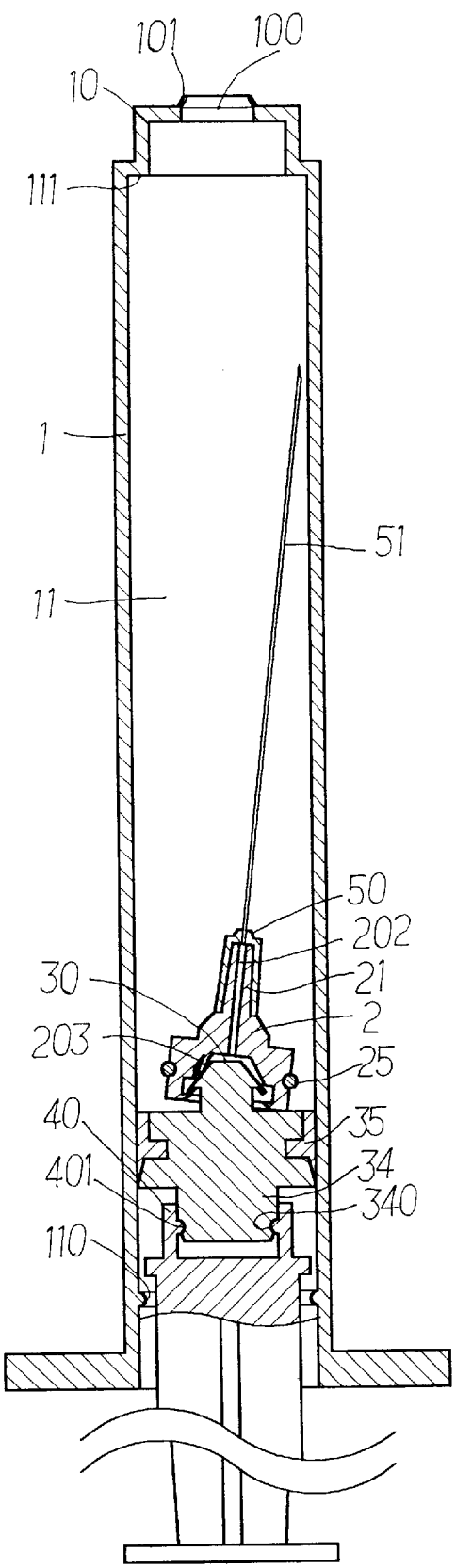
FIG·15
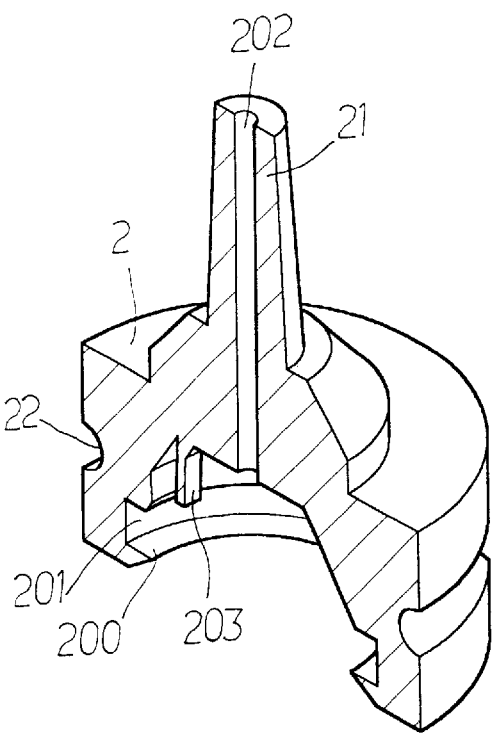
FIG·14

SYRINGE DEVICE

FIELD OF THE INVENTION

The present invention relates to a syringe device wherein the needle cannula is inclinedly retracted into the barrel by pulling the plunger after the medicine in the tube is injected.

BACKGROUND OF THE INVENTION

A conventional syringe device is shown in FIG. 1 and generally includes a barrel 10 with an engaging tube 12 extending from an end of the barrel 10. A stopper 17 is movably received in the barrel 10 and connected to a plunger 15 by a connection member 16 which is securely inserted into the stopper 17. A locking tip 180 is mounted to the engaging tube 12 and a needle cannula 181 is connected to the locking tip 180. Medicine in the interior 11 of the barrel 10 can be injected out from the needle cannula 181 by pushing the plunger 15 toward the engaging tube 12. A cap can be mounted to the locking tip to enclose the needle cannula 181. After being used, the syringe device has to be discarded and the needle cannula 181 together with the locking tip 180 are removed from the engaging tube 12. However, it is dangerous that when mounting the cap to enclose the needle cannula 181, the user could be cut by the needle cannula 181 and is therefore contaminated.

The present invention intends to provide a syringe device wherein the needle cannula is automatically retracted into the barrel by pulling the plunger away. from the needle cannular so that the users do not touch the needle cannula.

SUMMARY OF THE INVENTION

In accordance with one aspect of the present invention, there is provided a syringe device and comprising a barrel having an engaging section extending from a first end thereof. A hole is defined through the engaging section and a shoulder portion is defined in an inside of the first end of the barrel. A base member IS removably received in the engaging section and a tubular member extends from a first end of the base member and extending through the hole in the engaging section. A needle cannula is engaged with the tubular member. An engaging recess is defined in a second end of the base member and a first flange extends inward from a periphery defining the engaging recess. A stopper connected to a plunger is movably received in the barrel and a protrusion extends from the stopper. The protrusion is sized to engage with the engaging recess of the base member. A pushing means is located between the base member and the stopper so as to apply a force to the base member laterally when the base member is moved into the barrel when the plunger is pulled backward.

The primary object of the present invention is to provide a syringe device wherein the needle cannula is retracted into the barrel and a tip of the needle cannula contacts against the shoulder portion in the barrel.

These and further objects, features and advantages of the present invention will become more obvious from the following description when taken in connection with the accompanying drawings which show, for purposes of illustration only, several embodiments in accordance with the present invention.

BRIEF DESCRIPTION OF THE DRAWINGS

FIG. 10 is an illustrative view to show if the plunger is pushed again, the needle cannula is bent by the shoulder portion in the,barrel;

FIG. 11 is an illustrative view to show a cap can be received in the barrel;

FIG. 12 is a cross-sectional view to show another embodiment of the pushing means of the syringe device of the present invention;

FIG. 13 is an illustrative view to show if the plunger is pushed again from the status as shown in FIG. 12, the needle cannula is bent by the shoulder portion in the barrel, and FIG. 14 is an exploded view to show yet another embodiment of the pushing means of the syringe device of the present invention, and FIG. 15 is an illustrative view to show the base member and the needle cannula tilt in the barrel by the pushing means as shown in FIG. 14.

DETAILED DESCRIPTION OF THE PREFERRED EMBODIMENTS

Figure 1:
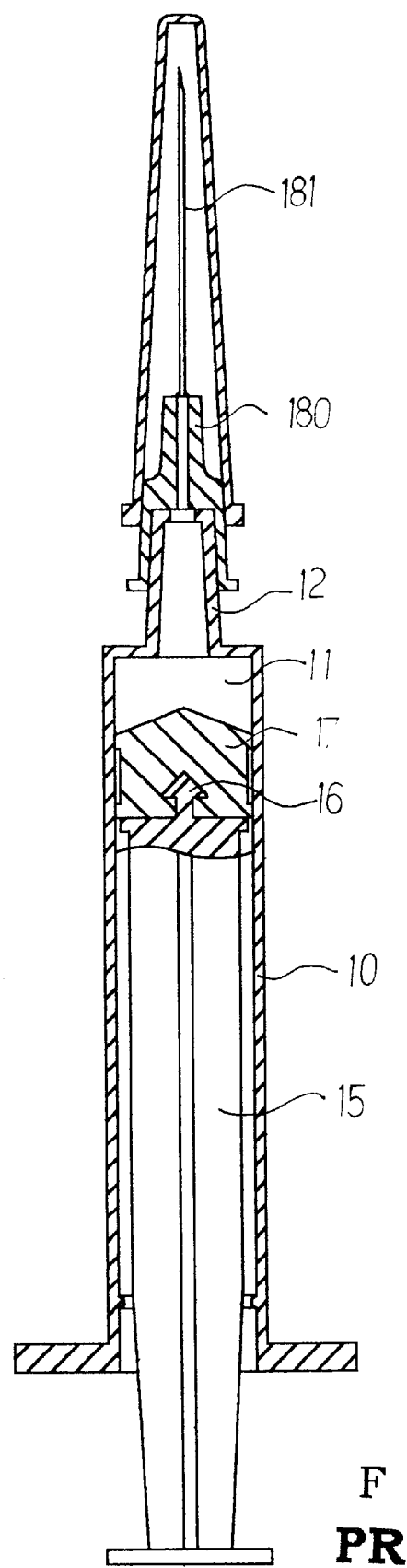
FIG. 1 is a cross-sectional view to show a conventional syringe device.
Figure 2:
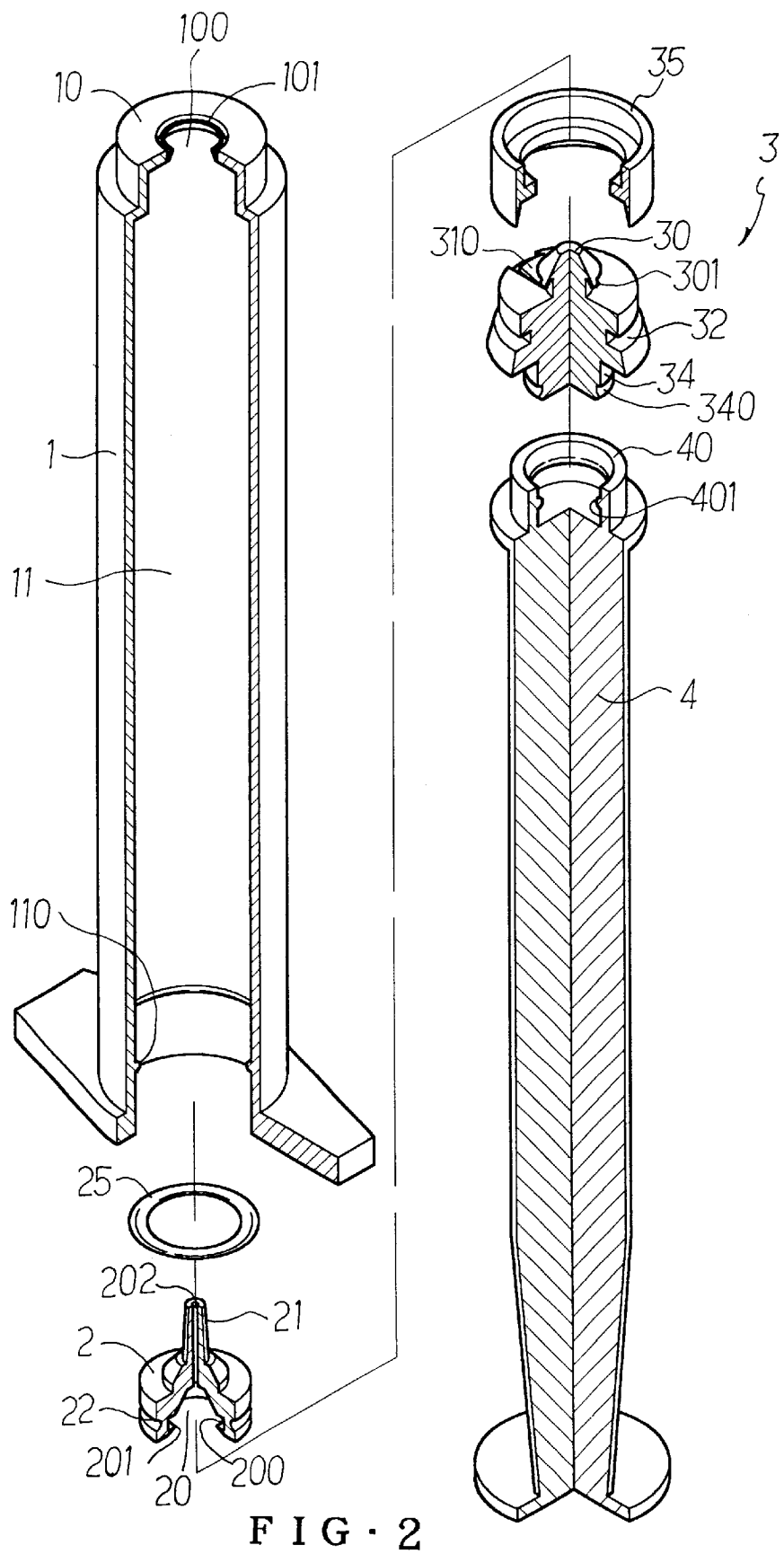
FIG. 2 is an exploded view to show a syringe device of the present invention.
Figure 3:
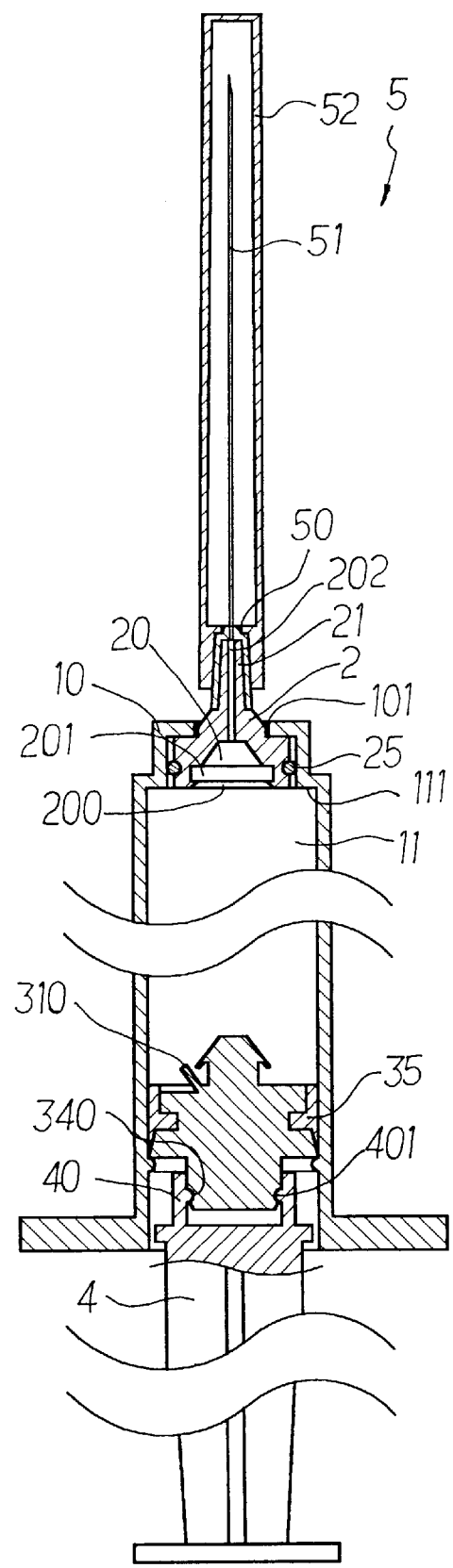
FIG. 3 is a cross-sectional view to show the syringe device when the plunger is not yet pushed.
Figure 4:
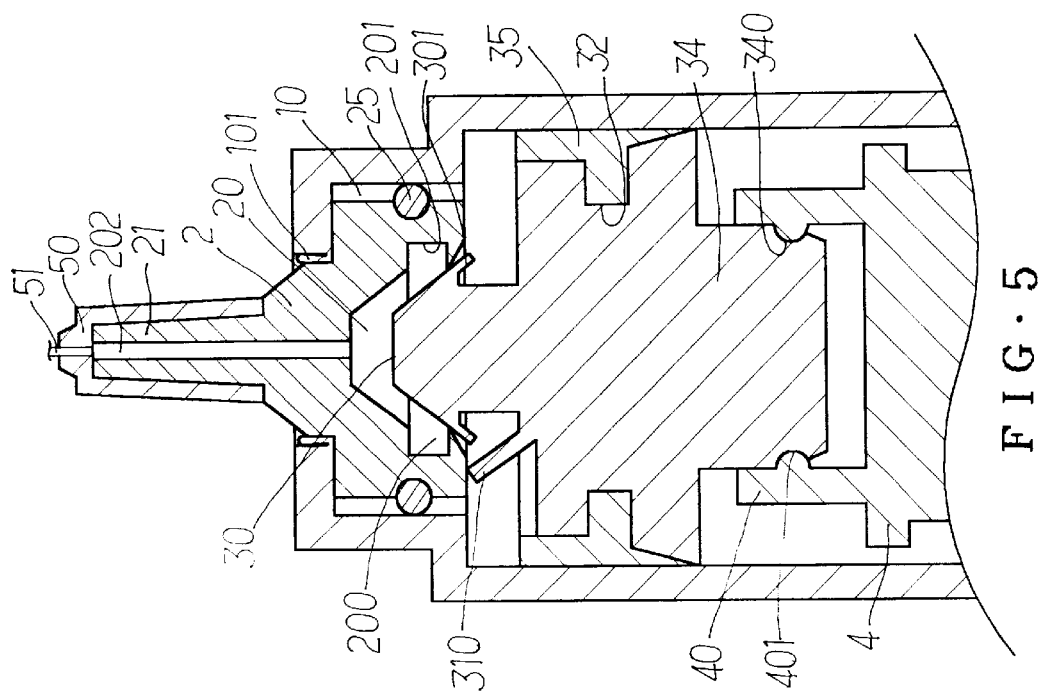
FIG. 4 is a cross-sectional view to show the syringe device of the present invention wherein the stopper is moved close to the base member.

Referring to FIGS. 2 and 3, the syringe device of the present invention comprises a barrel 1 having a first end with two finger flanges extending outward from the first end of the barrel 1 and an engaging section 10 extending from a second end of the barrel 10. A hole 100 is defined through the engaging section 10 and a shoulder portion 111 is defined in an inside of the second end of the barrel 1. A film 101 is connected to an inside of the engaging section 10 so as to seal the gap between a base member 2 received in the engaging section 10. The base member 2 is removably received in the engaging section 10 and a tubular member 21 extends from a first end of the base member 2. The tubular member 21 extends through the hole 100 in the engaging section 10 and a needle cannula 51 is engaged with the tubular member 21. A passage 202 is defined through the base member 2 and an engaging recess 20 is defined in a second end of the base member 2. The passage 202 communicates between the engaging recess 20 and the needle cannula 51. A first flange 200 extends inward from a periphery defining the engaging recess 20 and the first flange 200 has an inclined surface facing an interior 11 of the barrel 1. A groove 201 is defined in an inner periphery of the engaging recess 20 of the base member 2. In order to prevent leakage between the base member 2 and the inside of the engaging section 10, a seal 25 is mounted to the base member 2 and engaged with a groove 22 defined in an outer periphery of the base member 2. A cap 52 can be mounted to the tubular member 21 of the base member 2 and encloses the needle cannula 51.

A stopper 3 is movably received in the barrel 1. A protrusion 30 extends from a first end of the stopper 3 and a connection section 34 extends from a second end of the stopper 3. The connection section 34 has an annular groove 340 defined in an outside thereof for being connected with a plunger 4. The plunger 4 has an annular neck 40 extending from an end thereof and annular rib 401 extends from an inner periphery of the annular neck 40. The annular rib 401 is disengagably engaged with the annular groove 340. The protrusion 30 is sized to be engaged with the engaging recess 20 of the base member 2 and flexible plates 301 extend radially outward from the protrusion 30. An engaging groove 32 is defined in an outside of the stopper 3 and a sleeve 35 is mounted to the stopper 3. An annular flange extending inward from an inner periphery of the sleeve 35 and the annular flange is engaged with the engaging groove 32 of the stopper 3. The sleeve 35 ensures an airtight feature between the sleeve 35 and the barrel 1. A pushing means such as a lid 310 extends from the stopper 3 and urges the second end of the base member 2 when the protrusion 30 is engaged with the engaging recess 20 of the base member 2 as shown in FIG. 7.

Figure 5:
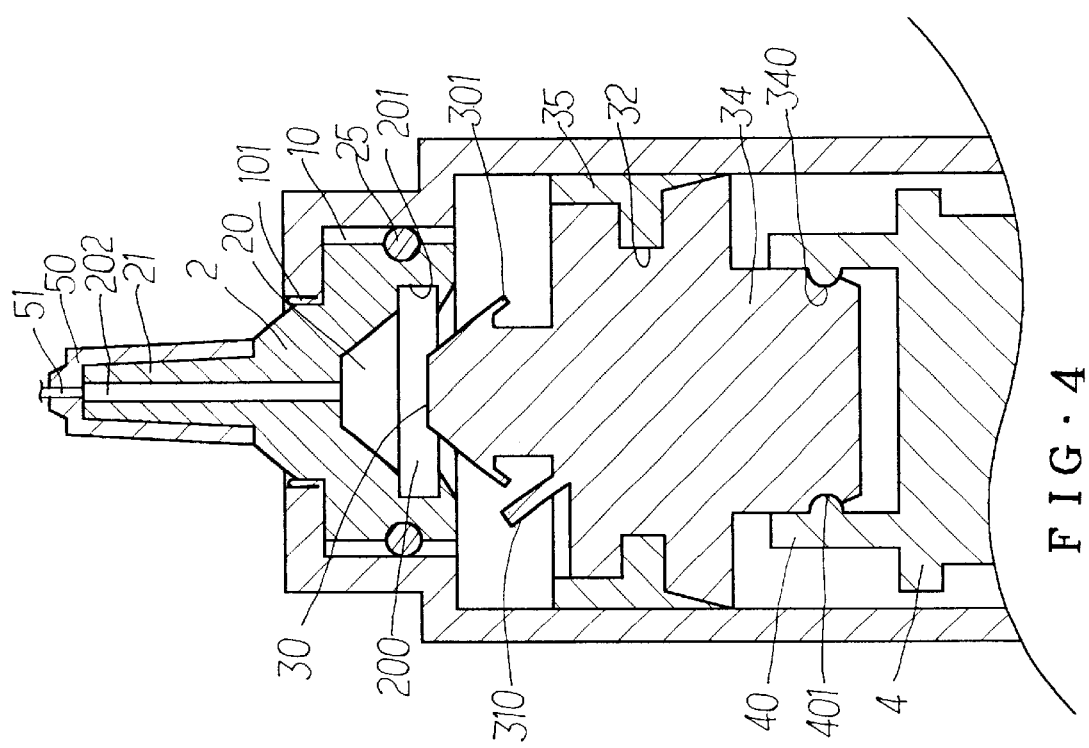
FIG. 5 is a cross-sectional view to show the syringe device of the present invention wherein the stopper is about to be engaged with the base member.
Figure 6:
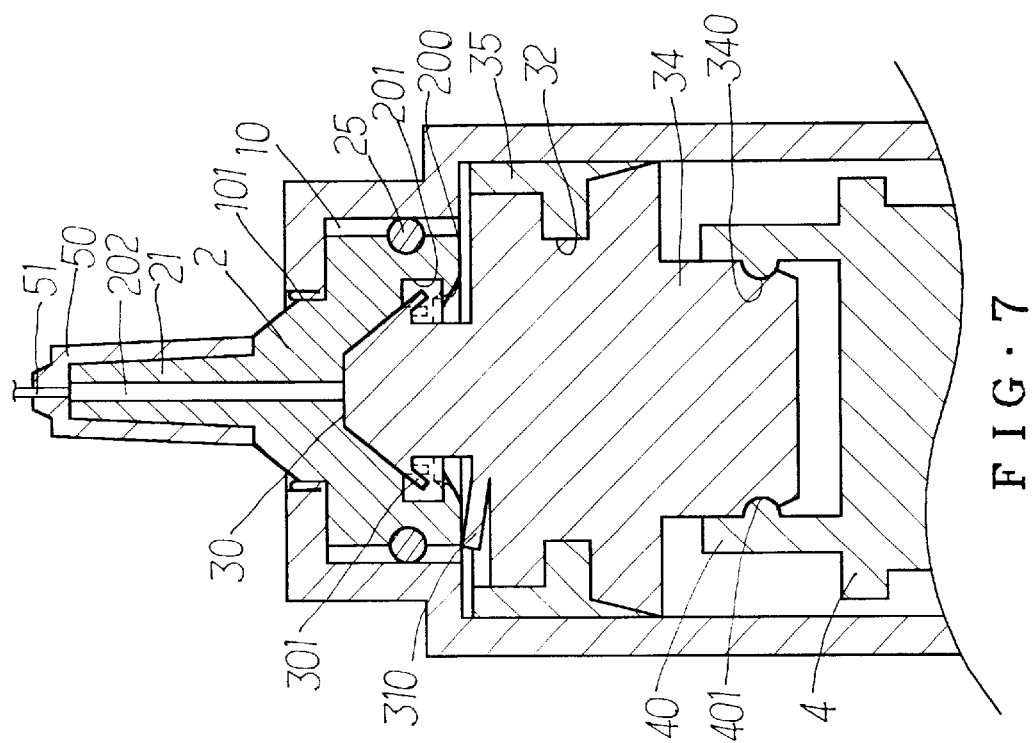
FIG. 6 is a cross-sectional view to show the syringe device of the present invention wherein the flexible plates of the stopper is deformed when the stopper is inserted into the recess of the base member.
Figure 7:
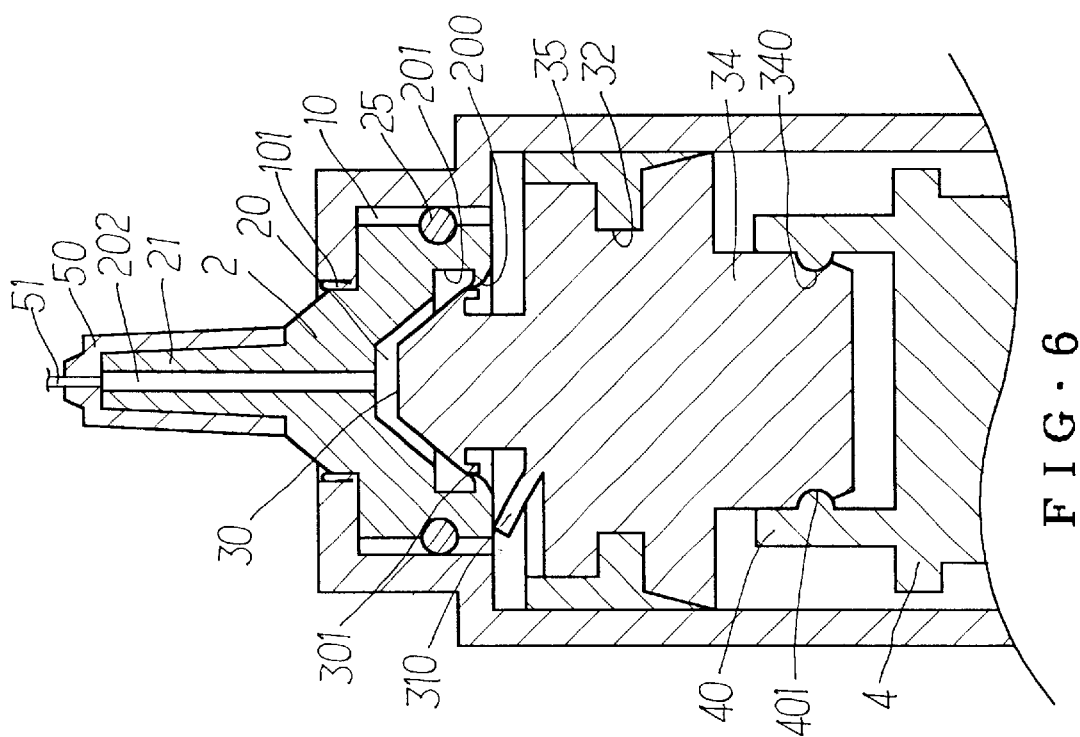
FIG. 7 is a cross-sectional view to show the syringe device of the present invention wherein the stopper is completely engaged with the recess of the base member.

Referring to FIGS. 4 to 7, when pushing the plunger 4 toward the base member 2 to inject medicine in the barrel 1 through the needle cannula 51, the taper-shaped protrusion 30 of the stopper 3 is inserted into the recess 20 and the flexible plates 301 are deformed when contacting the first flange 200 as shown in FIG. 5 and then the flexible plates 301 are engaged with the groove 201 after the flexible plates 301 pass over the first flange 200 as shown in FIGS. 6 and 7. The inclined surface of the first flange 200 facilitates the movement of the protrusion 30 of the stopper 3.

Figure 8:
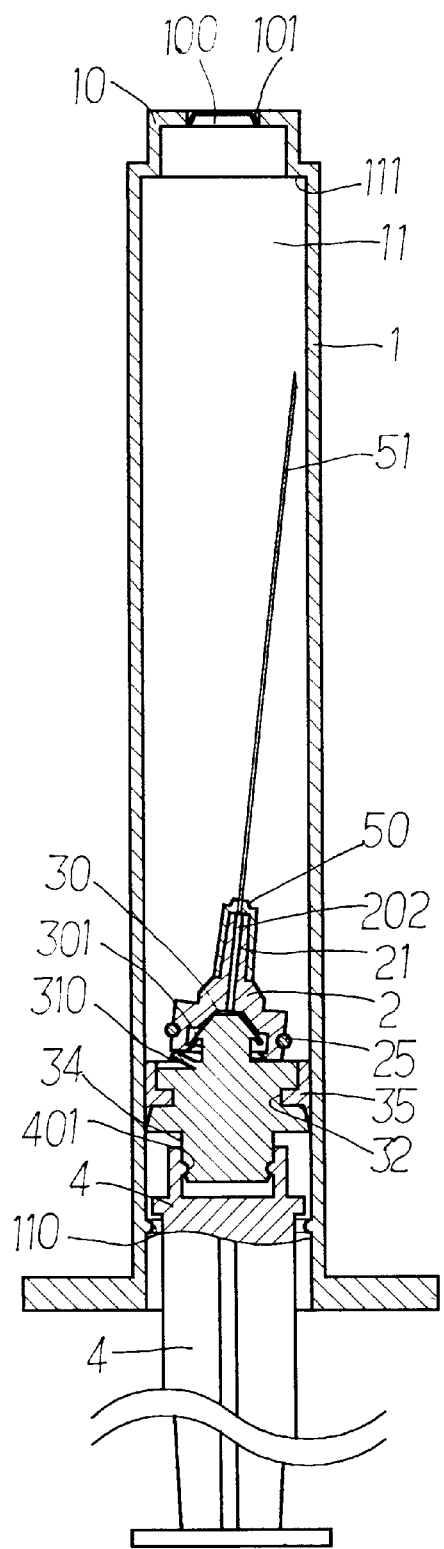
FIG. 8 is a cross-sectional view to show the base member and the needle cannula are received in the barrel when the plunger is pulled backward.
Figure 9:
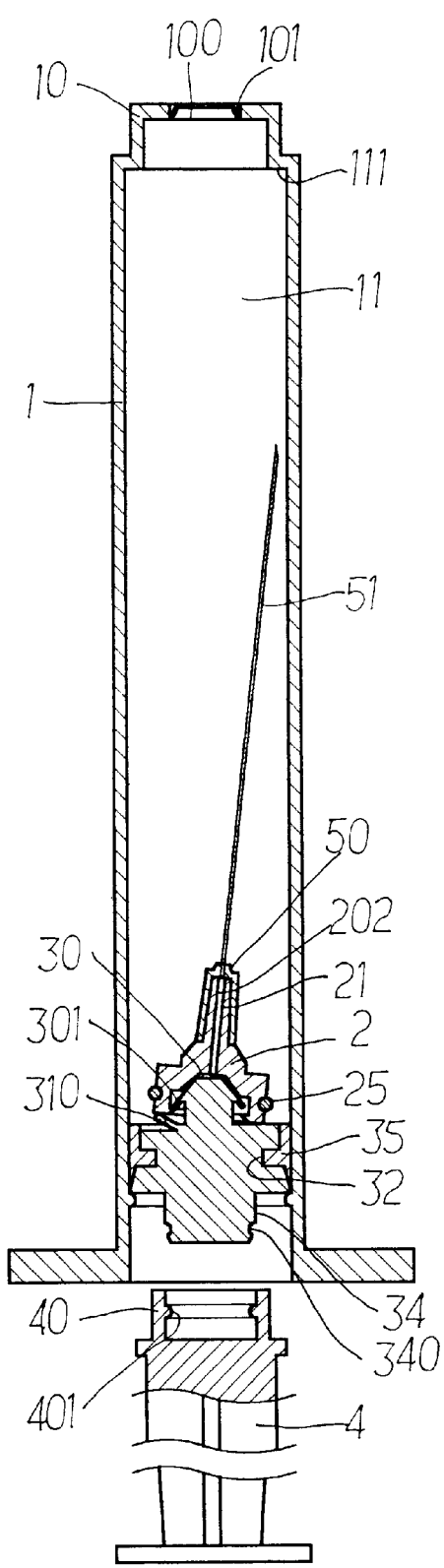
FIG. 9 is a cross-sectional view to show the plunger is disengaged from the stopper when the stopper is stopped by the second flange in the barrel.

After the plunger 4 is pushed to its extreme position and finishes the injection, the plunger 4 is pulled backward, the engaging force between the protrusion 30 and the base member 2 is larger than a friction between the seal 25 and the inner periphery of the engaging section 10, so that the base member 2 together with the needle cannula 51 are pulled to disengage from the engaging section 10 a shown in FIG. 8. When the base member 2 is disengaged from the engaging section 10, the lid 310 applies a force to the base member 2 laterally relative to an axis of the passage 202 of the base member 2 so that then base member 2 tilts. When the plunger 4 is continuously pulled, the stopper 3 is stopped by a second flange 110 extending radially inward from an inner periphery of the first end of the barrel 1, and the plunger 4 is separated from the connection section 34 of the stopper 3 as shown in FIG. 9. The second flange 110 prevents the stopper 3 from dropping from the barrel 1.

Referring to FIG. 10, if the plunger 4 is pushed again by whatever reasons, because the needle cannula 51 tilts in the barrel 1, the tip of the needle cannula 51 will contact the shoulder portion 111 of the barrel 1 and is deformed as shown. As shown in FIG. 11, the cap 52 may also be inserted into the barrel 1 from the hole 100 of the engaging section 10.

FIG. 12 shows that the pushing means is a lid 230 extending from the second end of the base member 2 and urges the stopper 3 when the protrusion 30 is engaged with the engaging recess 20 of the base member 2. The lid 230 will also tilts the base member 2 in the barrel 1. FIG. 13 shows that the needle cannula 51 is deformed if the plunger 4 is pushed again from the status as shown in FIG. 12.

The pushing means can also be a lid 203 extending from the inner periphery defining the engaging recess 20 of the base member 2 as shown in Fig, 14 and urges the protrusion 30 of the stopper 3 when the protrusion 30 is engaged with the engaging recess 20 of the base member 2. The lid 203 tilts the base member 2 when the base member 2 is moved in the barrel 1.

While we have shown and described various embodiments in accordance with the present invention, it should be clear to those skilled in the art that further embodiments may be made without departing from the scope and spirit of the present invention.

What is claimed:

1. A syringe device comprising:

a barrel having a first end and a second end, two finger flanges extending outward from said first end of said barrel and an engaging section extending from said second end of said barrel, a hole defined through said engaging section and a shoulder portion defined in an inside of said second end of said barrel;

a base member removably received in said engaging section and a tubular member extending from a first end of said base member, said tubular member extending through said hole in said engaging section, and a needle cannula engaged with said tubular member, a passage defined through said base member and an engaging recess defined in a second end of said base member, said passage communicating between said engaging recess and said needle cannula, a first flange extending inward from a periphery defining said engaging recess;

a stopper movably received in said barrel, a protrusion extending from a first end of said stopper and a connection section extending from a second end of said stopper, a plunger connected to said connection section, said protrusion being sized to engage with said engaging recess of said base member, and a pushing means located between said base member and said stopper and said pushing means applied a force to said base member laterally relative to an axis of said passage of said base member.

2. The syringe device as claimed in claim 1, wherein said stopper has flexible plates extending radially outward from said protrusion and a groove defined in an inner periphery of said engaging recess of said base member, said flexible plates engaged with said groove after said flexible plates pass over said first flange.

3. The syringe device as claimed in claim 2 wherein said first flange has an inclined surface facing an interior of said barrel.

4. The syringe device as claimed in claim 1, wherein said pushing means is a lid extending from said stopper and urges said second end of said base member when said protrusion is engaged with said engaging recess of said base member.

5. The syringe device as claimed in claim 1, wherein said pushing means is a lid extending from said second end of said base member and urges said stopper when said protrusion is engaged with said engaging recess of said base member.

6. The syringe device as claimed in claim 1, wherein said pushing means is a lid extending from said inner periphery defining said engaging recess of said base member and urges said protrusion of said stopper when said protrusion is engaged with said engaging recess of said base member.

7. The syringe device as claimed in claim 1 further comprising a second flange extending radially inward from an inner periphery of said first end of said barrel so as to prevent said stopper from dropping from said barrel.

8. The syringe device as claimed in claim 1, wherein said plunger has an annular neck extending from an end thereof and annular rib extending from an inner periphery of said annular neck, said connection section having an annular groove defined in an outside thereof and said annular rib disengagably engaged with said annular groove.

9. The syringe device as claimed in claim 1 further comprising an engaging groove defined in an outside of said stopper and a sleeve mounted to said stopper, an annular flange extending inward from an inner periphery of said sleeve and said annular flange engaged with said engaging groove of said stopper.

* * * * *